United States Patent [19]

Henderson et al.

[11] Patent Number: 4,828,827

[45] Date of Patent: May 9, 1989

[54] PROCESS FOR AUGMENTING SOFT TISSUE WITH CROSS-LINKED POLYVINYL PYRROLIDONE

[75] Inventors: Alex M. Henderson; Loretta M. McKey, both of Peterborough; A. Kim Gordon, Oshawa, all of Canada

[73] Assignee: Ethicon, Inc., Somerville, N.J.

[21] Appl. No.: 940,899

[22] Filed: Dec. 12, 1986

[51] Int. Cl.⁴ .............................................. A61K 31/79
[52] U.S. Cl. ..................................................... 424/80
[58] Field of Search ........................................... 424/80

[56] References Cited

U.S. PATENT DOCUMENTS

| | | | |
|---|---|---|---|
| 3,943,045 | 3/1976 | Cordrey et al. | 424/423 X |
| 3,949,073 | 4/1976 | Daniels et al. | 424/177 |
| 4,391,797 | 7/1983 | Folkman et al. | 424/19 |

Primary Examiner—Leonard Schenkman
Attorney, Agent, or Firm—Charles J. Metz

[57] ABSTRACT

An aqueous gel of cross-linked polyvinyl pyrrolidone is used to augment soft tissue in a mammal.

8 Claims, No Drawings

PROCESS FOR AUGMENTING SOFT TISSUE WITH CROSS-LINKED POLYVINYL PYRROLIDONE

This invention relates to a method for augmenting soft tissue in mammals, including humns, with cross-linked polyvinyl pyrrolidone.

BACKGROUND OF THE INVENTION

Soft tissue augmentation for cosmetic purposes and to repair congenital or trauma-caused defects is a growing technique in the medical profession. Solid or liquid silicone implants have been used for some years, and more recently, a collagen preparation ("Zyderm") that is specifically described in Daniels et al., U.S. Pat. No. 3,949,073, has been used in cosmetic facial repair to remove wrinkles, etc. The silicone implants have never been entirely satisfactory because they tend to harden or calcify, and the collagen preparation elicits an inflammatory immune response in a small but significant number of patients. The collagen treatment is usually not permanent, so it must often be repeated periodically, e.g., every 12 to 24 months. An inflammatory immune response is sometimes elicited with collagen upon retreatment, even if it was absent in earlier treatments. [Ref., Webster et al., Arch. Otolaryngol., 110, 656(1984), Cohen et al., Plast. Reconst. Surg., 73(5), 857(1984), and Aran et al., Plast. Reconst. Surg., 71(5), 731(1983).]

The present invention is based on the discovery that crosslinked polyvinyl pyrrolidone ("PVP") can be used to augment soft tissue in mammals, including humans, to treat defects therein, with a remarkable lack of tissue reaction. The treatment is long-lasting, if not permanent, so the need to re-treat as one must do in most cases with collagen, is much reduced if not eliminated entirely.

BRIEF SUMMARY OF THE INVENTION

The process of the invention comprises administering to a soft tissue site in a mammal, including humans, in need of augmentation, an aqueous gel of crosslinked PVP.

THE PRIOR ART

Cross-linked vinyl pyrrolidone polymers are known. See for instance, Folkman et al., U.S. Pat. No. 4,391,797 (col. 1, line 68) and Cordrey et al., U.S. Pat. No. 3,943,045, who disclose the use of crosslinked vinyl pyrrolidone copolymers as contact lenses, prosthetic devices, surgical implants, protective corneal fittings, and protective membranes or bandages.

Seiderman, in U.S. Pat. No. 3,966,847, discloses contact lenses made of crosslinked vinyl pyrrolidone copolymers.

Boghosian, in U.S. Pat. No. 3,150,045, discloses the use of uncrosslinked PVP in aqueous solution as a material to stimulate growth of epithelial cells in the eye.

Amkraut et al., in U.S. Pat. No. 4,439,199, disclose the use of uncrosslinked PVP as a delivery system for immunopotentiator medicaments.

The use of collagen or cartilage based materials to augment soft tissue is disclosed in U.S. Pat. Nos. 3,949,073 (Daniels et al.), 4,424,208 (Wallace et al.), and 4,469,676 (Hecmati).

DETAILED DESCRIPTION OF THE INVENTION

Polyvinyl pyrrolidone is commercially available as a high melting water soluble polymeric powder in viscosity ranges which correspond to number average molecular weights from 10,000 to 700,000. It is sold under a variety of trade names: Povidone, PVP, Plasdone, and Kollidon are examples. These powders are hygroscopic and generally contain about 5% water. There are purified grades available which are used in the pharmaceutical industry and as blood plasma volume extenders. (Encyclopedia of Polymer Science and Technology, Vol. 14, "N-Vinyl Amide Polymers", H. F. Mark, N. G. Gaylord, N. M. Bikales, Eds., J. Wiley and Sons, New York, (1964), pp. 239-251). Solutions of PVP in an aqueous carrier can be subjected to ionizing radiation, preferably gamma rays, and crosslinked into insoluble swollen gels. The concentration range suitable for producing homogeneous soft gels suitable for use as a soft tissue filler implant is 5-40%, and preferably 10-20%, by weight of the solution. Concentrations of less than 5% PVP tend to produce heterogeneous systems as the amount of water in the system is too great to be included in the gel structure. The type of ionizing radiation used to produce crosslinking is preferably gamma rays in the range of 2-15 Mrad dose, preferably 2.4-3.4 Mrad.

The PVP is dissolved in the aqueous carrier and then the solution is loaded into a syringe equipped with a 26 gauge or smaller needle and subjected to irradiation. After the irradiation treatment the gel is sterile and ready for use, for example, for injection under a wrinkle to plump up the skin.

Optionally, the PVP solution can be irradiated in a glass ampoule, flask, or vial and then transferred to a syringe fitted with a 26 gauge or smaller needle, and sterilized, for example, by subjecting the gel to heat treatment of 70°-75° C. for 6 hours before use. This heat treatment has no noticeable effect on the consistency of the PVP hydrogel. This treatment is presented as an example only and is not meant to limit the scope of the invention.

As the concentration of PVP is increased from 5 to 40% by weight in the aqueous carrier, the gels become softer and less friable. An explanation of this phenomenon, which is not meant to limit the scope of the invention, is that a particular dose of ionizing radiation will produce a given number of crosslinks. As the concentration of polymer chains increases, the number of crosslinks per chain decreases and a looser network forms. Therefore, it is possible to alter the consistency of the hydrogels by manipulating concentrations of polymer or other additives which change the crosslink density or by changing the total dose of irradiation. The consistency of several hydrogels is given in Table I, below.

IN VIVO STUDIES

In order to determine the permanence and consistency of PVP hydrogel in vivo, a relatively large quantity (0.25 cc) was injected into the rat dorsal subcutis. Adult female Woodlyn Wistar albino rats were used. All rats were held in the animal colony for at least one week prior to being employed in the study. They were maintained according to the guidelines set down by the Canadian Association for Laboratory Animal Sciences and had food and water ad libitum. All implantation procedures were carried out with the test animals under general anesthesia (Metofane). The abdominal skin of the rat was shaved, washed with GAMOPHEN* leaves and painted with IOPREP*.
*TM-Arbrook Inc., Arlington, Tex., USA Injections of the sterile PVP hydrogels (dry heat sterilized at 70°-75° C. for 6 hours) were made in the abdominal subcutis from pre-loaded syringes equipped with hypodermic needles. All injections were 0.25 cc in size. Injections of commercial ZYDERM* collagen based soft tissue filler were made in the exact same manner to serve as controls. The observation procedures involved first the evaluation of the gross tissue response and then the estimation of absorption having occurred. In order to accomplish this the test animals were placed under light general anesthesia (Metofane). Transillumination of the abdominal skin was employed to evaluate the tissue response. Progressive measurement of the sizes of the implants were taken and recorded in order to determine absorption patterns. At the end of this study the implants were examined histologically. The results of this study are described below in Tables II and III.

In another study of long term in vivo performance and tissue response, small volume injections (<0.1 cc) of a 13% PVP gel and ZYDERM* were made in the dorsal skin of rats. The PVP was injected to the left of the spinal column and the ZYDERM to the right of the spinal column. An attempt was made to inject the samples intradermally, although subsequent histological analysis showed sample present in the dermis, the hypodermis, and the subcutis (Table IV, below).

The following examples are provided to illustrate embodiments of the invention.
*TM-Collagen Corporation, Palo Alto, CA, USA

EXAMPLE 1

Samples of polyvinyl pyrrolidone (MW=44,000) from two lots were dissolved in distilled water to produce solutions of concentrations ranging from 4.9%, 10%, 13%, and 20%, based on total solution weight. The solutions were stored in glass ampoules and irradiated to 2.5 Mrad in a $Co^{60}$ gamma irradiator. Transparent gels were formed and their appearance and consistency as well as viscosity characterization of the starting polymer are described in Table I.

TABLE I

Characterization of Polyvinylpyrrolidone and PVP Hydrogels

| PVP Inherent Viscosity* | PVP Type | Concentration of Gel | Consistency of Hydrogel** |
|---|---|---|---|
| 0.186 dl/g | MW = 44,000 old lot | 20% | clear, rubbery |
| 0.167 dl/g | MW = 44,000 Lot 88568 | 4.9% | clear, rubbery but friable |
| 0.167 dl/g | MW = 44,000 Lot 88568 | 10% | clear, rubber, less stiff than 5% gel |
| 0.167 dl/g | MW = 44,000 Lot 88568 | 13% | clear, more gelatinous, softer than 5% and 10% gel |
| 0.179 dl/g | GAF Plasdone K-29-32 Lot G1090GB | 15% | clear, very similar to 13% BDH gel |
| 0.697 dl/g | MW = 700,000 Lot 97300030F | 15% | clear, stiff rubber, friable |
| 0.168 dl/g | GAF Plasdone NP-K30 | 3% | opaque gel, excluded 50% of the water, friable |
| 0.186 | BDH MW = 44,000 Old Lot | 2.7% | opaque gel, excluded 50% of the water |

*5% solutions in distilled water
**PVP solution irradiated to 2.5 Mrad in $Co^{60}$ source

EXAMPLE 2

The gels of Example 1 of concentration 4.9% and 13% were loaded into 10 cc hypodermic needles and heat sterilized at 70°-75° C. for six hours. These gels were then implanted into the subcutis of rats and their permanence and tissue response studied as described in Tables II and III. The 13% gels were also injected into the dermis, and subcutis of rates and studied as described in Table IV.

TABLE II

In Vivo Evaluations of Soft Tissue Fillers: Consistency, Tissue Response, and Absorption of 0.25 cc Implants in the Ventral Subcutis of Rats

| Sample | Time Period | Consistency* | Tissue Response | Absorption** |
|---|---|---|---|---|
| Zyderm | 1 day | fibrous 3 | minimal | shrinkage, resorption of water |
| " | 1 week | fibrous 3 | minimal | none |
| " | 12 weeks | fibrous 2 | none | 10% |
| " | 16 weeks | softer-fibrous 2 | none | 75% |
| 13% PVP Hydrogel | 1 day | liquidy 3 | slight | none |
| 13% PVP Hydrogel | 1 week | softer-liquidy 2 | minimal | " |
| 13% PVP Hydrogel | 12 weeks | liquidy 2 | minimal | " |
| 13% PVP Hydrogel | 16 weeks | gelatinous 2 | negligible | " |
| 4.9% PVP Hydrogel | 1 day | gelatinous 3 | slight | 25% |
| 4.9% PVP Hydrogel | 1 week | liquidy 1 | minimal | " |
| 4.9% PVP Hydrogel | 12 weeks | gelatinous 2 | minimal | 50% |
| 4.9% PVP Hydrogel | 16 weeks | gelatinous 2 | minimal | 50% |

*Scale: 3 = firm; 1 = very soft
**Estimated by measuring diameter and depth of implant with a ruler

TABLE III

Histological Evaluation of Soft Tissue Filler Implants 0.25 cc Implants in the Ventral Subcutis of Rats

| Time Period | 13% PVP Hydrogel | Zyderm |
|---|---|---|
| 1 year subcutis | Present in the subcutis soft tissue filler well invaded by collagen, fibrous tissue, and fibroblasts no significant encapsulation was evident an the implants remained soft to the touch | present in the no apparent absorption no encapsulation |

TABLE VI

Histological Evaluation of Soft Tissue Filler Implants 0.1 cc 'Intradermal' Implants in the Dorsal Sin of Rats

| Time Period | 13% Hydrogel | Zyderm |
| --- | --- | --- |
| 1 day | present in the subcutis and in somewhat globular form surrounded in active fibroblasts | N/A* |
| 1 week | present in globular form in subcutis and hypodermis tissue reaction minimal to slight globules surrounded by thin layers of tissue reaction cells | Present in subcutis and hypodermis tissue reaction minimal no significant cellular infiltration implant present as one continuous mass (not globular) |
| 4 weeks | same as 1 week | present in subcutis surrounded by thin layer of connective tissue no replacement or absorption of Zyderm |
| 12 weeks | present in subcutis slight encapsulation of implant with delicate strands of collagen and elastin having been laid down by fibro blasts implant remained soft to touch | present in subcutis small amount of encapsulation no absorption |
| 36 weeks | present in a globular form in subcutis and hypodermis no apparent absorption collagen fibres surrounded the implant | N/A |
| 1 year | present in the hypodermis no fibrous invasion evident no significant encapsulation and implants remained soft to touch | N/A |

*N/A = not available
Implanted by injection through 26 g needle

EXAMPLE 3

One half gram samples of the 4.9% and 13% gels of Example I were stored in 25 ml of phosphate buffer solution (pH=7.4) at 50° C. for two weeks. The gels appeared unchanged except for minor swelling at the end of this time period.

EXAMPLE 4

Samples of polyvinyl pyrrolidone (MW=44,000) from one of the lots described in Example 1 was dissolved in distilled water to produce solutions of concentrations 1% and 2%. The solutions were loaded into glass vials and irradiated to 2.5 Mrad dose in a $Co^{60}$ irradiator. The gels formed were opaque and had excluded water which could be decanted from the gel. The water was removed from the 2% gel in a forced air oven and the actual solids content measured to be 2.7%.

EXAMPLE 5

A sample of pharmaceutical grade PVP, Plasdone K 29-32, was dissolved in distilled water to produce a 15% w/w solution. This was loaded into a glass vial and irradiated in a $Co^{60}$ irradiator to a 2.5 Mrad dose. This produced a transparent gel similar in consistency to the 13% gel produced in Example 1.

EXAMPLE 6

A sample of 700,000 M.W. PVP was dissolved in distilled water to produce a 15% w/w solution. This was irradiated as in Example 5. A transparent gel was produced which was stiffer and more friable than the gels of Examples 1 and 5.

EXAMPLE 7

A sample of 44,000 M.W. PVP was dissolved in distilled water to produce a 40% w/w solution. This sample was loaded into a glass ampoule and irradiated to 5 Mrad in a $Co^{60}$ gamma irradiator. A transparent gel was formed which was firmer than the samples prepared in Example 1.

EXAMPLE 8

A sample of 360,000 M.W. PVP was dissolved in distilled water to produce a 15% w/w solution. This sample was loaded into a glass ampoule and irradiated to a 2.5 Mrad in a $Co^{60}$ gamma irradiator. A transparent gel was formed which was stiffer and more friable than the gels produced in Examples 1 and 5.

EXAMPLE 9

A sample of 700,000 M.W. PVP was dissolved in distilled water to produce a 40% w/w solution. This was loaded into a glass ampoule and irradiated to 2.5 Mrad in a $Co^{60}$ gamma irradiator. A transparent gel formed.

EXAMPLE 10

A sample of 10,000 M.W. PVP from Polysciences Inc. was dissolved in distilled water to produce a 5% w/w solution. The solution was loaded into a glass ampoule and irradiated to 15 Mrad in a $Co^{60}$ gamma irradiator. A soft transparent gel formed.

What is claimed is:

1. In a process for augmenting soft tissue in a living mammal which comprises administering a sterile implant to the mammal at the site of augmentation, the improvement which comprises employing as said implant a sterile aqueous gel consisting essentially of cross-linked polyvinyl pyrrolidone, said cross-linked polyvinyl pyrrolidone being present in said gel in a concentration of from about 5 to about 40 percent, by weight.

2. The process of claim 1 wherein said sterile gel is administered by injection.

3. The process of claim 1 wherein the gel is produced by subjecting an aqueous solution of polyvinyl pyrrolidone to ionizing radiation.

4. The process of claim 3 wherein the ionizing radiation is gamma rays from a $Co^{60}$ source.

5. The process of claim 3 wherein the concentration of polyvinyl pyrrolidone in the aqueous solution is within the range of from 5 to 40 percent by weight, based on total weight of the solution.

6. The process of claim 5 wherein said concentration is within the range of from 12 to 20 percent, by weight.

7. The process of claim 4 wherein the total dose of radiation is from 2 to 15 Mrads.

8. The process of claim 7 wherein the total dose of radiation is from 2.4 to 3.4 Mrads.

* * * * *